US008067350B2

(12) United States Patent
Wenzel et al.

(10) Patent No.: US 8,067,350 B2
(45) Date of Patent: Nov. 29, 2011

(54) COLOR CHANGING CLEANSING COMPOSITION

(75) Inventors: Scott W. Wenzel, Neenah, WI (US); Corey Thomas Cunningham, Larsen, WI (US); Katherine D. Stahl, Appleton, WI (US); David William Koenig, Menasha, WI (US); Kelly Davis Arehart, Roswell, GA (US); John Gavin MacDonald, Decatur, GA (US); Brendon F. Ribble, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 433 days.

(21) Appl. No.: 11/796,615

(22) Filed: Apr. 27, 2007
(Under 37 CFR 1.47)

(65) Prior Publication Data

US 2008/0234160 A1  Sep. 25, 2008

Related U.S. Application Data

(63) Continuation-in-part of application No. 11/303,009, filed on Dec. 15, 2005, now abandoned.

(51) Int. Cl.
*C11D 3/40* (2006.01)
*C11D 3/60* (2006.01)

(52) U.S. Cl. ........ 510/130; 510/159; 510/473; 510/474; 510/480; 510/491; 510/507; 510/511

(58) Field of Classification Search .................. 510/130, 510/473, 474, 491, 507, 511, 159, 480
See application file for complete search history.

(56) References Cited

U.S. PATENT DOCUMENTS

| | | | |
|---|---|---|---|
| 2,445,994 A | 7/1948 | Benson et al. |
| 2,496,270 A | 2/1950 | Coler |
| 3,042,621 A | 7/1962 | Kirschenbauer |
| 3,584,115 A | 6/1971 | Gebhart et al. |
| 3,600,060 A | 8/1971 | Churchill |
| 3,619,254 A | 11/1971 | Davis |
| 3,650,831 A | 3/1972 | Jungermann et al. |
| 3,658,985 A | 4/1972 | Olson, Jr. et al. |
| 3,669,891 A | 6/1972 | Greenwood et al. |
| 3,755,064 A | 8/1973 | Maierson |
| 3,769,398 A | 10/1973 | Hewitt |
| 3,770,641 A | 11/1973 | Cantor et al. |
| 3,849,241 A | 11/1974 | Butin et al. |
| 3,926,830 A | 12/1975 | Horiguchi et al. |
| 3,935,129 A | 1/1976 | Jabalee |
| 4,000,317 A | 12/1976 | Menda et al. |
| 4,013,787 A | 3/1977 | Varlerberghe et al. |
| 4,015,937 A | 4/1977 | Miyamoto et al. |
| 4,016,089 A | 4/1977 | Regan et al. |
| 4,022,706 A | 5/1977 | Davis |
| 4,028,118 A | 6/1977 | Nakasuji et al. |
| 4,038,148 A | 7/1977 | Miller et al. |
| 4,070,510 A | 1/1978 | Kahn |
| 4,110,426 A | 8/1978 | Barnhurst et al. |
| 4,128,508 A | 12/1978 | Munden |
| 4,129,515 A | 12/1978 | Foster |
| 4,145,413 A | 3/1979 | Usdin et al. |
| 4,150,106 A | 4/1979 | Assal et al. |
| 4,154,706 A | 5/1979 | Kenkare et al. |
| 4,169,811 A | 10/1979 | Yoshikawa et al. |
| 4,174,292 A | 11/1979 | Seidenberger et al. |
| 4,193,888 A | 3/1980 | McHugh |
| 4,224,195 A | 9/1980 | Kawasaki et al. |
| 4,248,597 A | 2/1981 | McNeely |
| 4,257,188 A | 3/1981 | Barker |
| 4,259,204 A | 3/1981 | Homma |
| 4,311,479 A | 1/1982 | Fenn et al. |
| 4,313,393 A | 2/1982 | Barbuscio et al. |
| 4,329,334 A | 5/1982 | Su et al. |
| 4,329,335 A | 5/1982 | Su et al. |
| 4,329,336 A | 5/1982 | Su et al. |
| 4,349,509 A | 9/1982 | Yoshikawa et al. |
| 4,368,147 A | 1/1983 | Inamorato et al. |
| 4,381,920 A | 5/1983 | Garlen |
| 4,412,959 A | 11/1983 | Wegner et al. |
| 4,450,091 A | 5/1984 | Schmolka |
| 4,472,507 A | 9/1984 | Pluim, Jr. |
| 4,499,001 A | 2/1985 | Eoga |
| 4,526,701 A | 7/1985 | Rubin |
| 4,595,526 A | 6/1986 | Lai |
| 4,678,658 A | 7/1987 | Casey et al. |
| 4,678,704 A | 7/1987 | Fellows |
| 4,690,815 A | 9/1987 | Deckner |
| 4,696,258 A | 9/1987 | Magrath et al. |

(Continued)

FOREIGN PATENT DOCUMENTS

EP  0047101 A2  3/1982
(Continued)

OTHER PUBLICATIONS

International Search Report for PCT/IB2008/050775, mailed Mar. 3, 2008-13 pages.

(Continued)

*Primary Examiner* — Lorna M Douyon

(74) *Attorney, Agent, or Firm* — Dority & Manning, P.A.

(57) ABSTRACT

A cleansing composition is disclosed that changes color during use. The cleansing composition contains a plurality of thermochromic dyes that cause a color change to occur at a threshold temperature and continue to cause a color change over a temperature range. The range of temperatures corresponds to approximately the amount of time sufficient to properly wash or scrub using the product.

16 Claims, No Drawings

U.S. PATENT DOCUMENTS

| | | | |
|---|---|---|---|
| 4,717,710 A * | 1/1988 | Shimizu et al. | 503/213 |
| 4,725,462 A | 2/1988 | Kimura | |
| 4,756,906 A | 7/1988 | Sweeny | |
| 4,793,988 A | 12/1988 | Casey et al. | |
| 4,818,491 A | 4/1989 | Fariss | |
| 4,889,728 A | 12/1989 | Maeda et al. | |
| 4,896,144 A | 1/1990 | Bogstad | |
| 4,906,395 A | 3/1990 | Stoesser et al. | |
| 4,917,814 A | 4/1990 | MacIntyre et al. | |
| 4,921,636 A | 5/1990 | Traas | |
| 4,930,506 A | 6/1990 | Ullrich | |
| 4,954,544 A | 9/1990 | Chandaria | |
| 4,957,949 A | 9/1990 | Kamada et al. | |
| 4,960,585 A | 10/1990 | Tehrani | |
| 4,965,063 A | 10/1990 | Casey et al. | |
| 5,037,843 A | 8/1991 | Schoenberg | |
| 5,057,303 A | 10/1991 | Casey | |
| 5,064,635 A | 11/1991 | Casey | |
| 5,110,492 A | 5/1992 | Casey | |
| 5,203,327 A | 4/1993 | Schoendorfer et al. | |
| 5,213,881 A | 5/1993 | Timmons et al. | |
| 5,279,735 A | 1/1994 | Cosentino et al. | |
| 5,320,835 A | 6/1994 | Pahlck et al. | |
| 5,380,528 A | 1/1995 | Alban et al. | |
| 5,382,433 A | 1/1995 | Pahlck et al. | |
| 5,420,118 A * | 5/1995 | Alban et al. | 514/63 |
| 5,427,708 A | 6/1995 | Stark | |
| 5,431,697 A | 7/1995 | Kamata et al. | |
| 5,443,987 A | 8/1995 | DeCicco et al. | |
| 5,460,647 A | 10/1995 | Snedeker et al. | |
| 5,460,805 A | 10/1995 | Davis et al. | |
| 5,466,465 A | 11/1995 | Royds et al. | |
| 5,478,361 A | 12/1995 | Sumii et al. | |
| 5,482,654 A | 1/1996 | Luttrell et al. | |
| 5,486,228 A | 1/1996 | Miller et al. | |
| 5,503,583 A | 4/1996 | Hippely et al. | |
| 5,523,075 A | 6/1996 | Fuerst et al. | |
| 5,554,361 A | 9/1996 | Dixon | |
| 5,567,420 A | 10/1996 | McEleney et al. | |
| 5,581,090 A | 12/1996 | Goudjil | |
| 5,591,255 A | 1/1997 | Small et al. | |
| 5,595,754 A | 1/1997 | Ito et al. | |
| 5,597,556 A | 1/1997 | Moghe et al. | |
| 5,612,222 A | 3/1997 | Gordon et al. | |
| 5,612,541 A | 3/1997 | Hoffmann et al. | |
| 5,616,722 A | 4/1997 | Schoenberg et al. | |
| 5,667,798 A | 9/1997 | Royds et al. | |
| 5,670,469 A | 9/1997 | Dingus et al. | |
| 5,680,962 A | 10/1997 | McEleney et al. | |
| 5,690,945 A * | 11/1997 | Bui-Bertrand et al. | 424/401 |
| D388,990 S | 1/1998 | Brandenburg et al. | |
| 5,741,592 A | 4/1998 | Lewis et al. | |
| 5,753,210 A | 5/1998 | McEleney et al. | |
| 5,753,244 A | 5/1998 | Reynolds et al. | |
| 5,784,162 A | 7/1998 | Cabib et al. | |
| 5,792,047 A | 8/1998 | Coggins | |
| 5,792,384 A | 8/1998 | Warren | |
| 5,793,292 A | 8/1998 | Ivey, Jr. | |
| 5,837,645 A | 11/1998 | Fuerst et al. | |
| 5,842,905 A | 12/1998 | Lee et al. | |
| 5,858,340 A * | 1/1999 | Briggs et al. | 424/70.19 |
| 5,876,995 A | 3/1999 | Bryan | |
| 5,900,067 A | 5/1999 | Jones | |
| 5,910,421 A | 6/1999 | Small, Jr. et al. | |
| 5,929,004 A | 7/1999 | Ushijima et al. | |
| 5,939,088 A | 8/1999 | Ito et al. | |
| 5,939,485 A | 8/1999 | Bromberg et al. | |
| 5,942,438 A | 8/1999 | Antonoplos et al. | |
| 5,942,478 A * | 8/1999 | Lopes | 510/130 |
| 5,952,275 A | 9/1999 | Feferman et al. | |
| 5,955,062 A | 9/1999 | McEleney et al. | |
| 5,958,383 A | 9/1999 | McEleney et al. | |
| 5,971,827 A | 10/1999 | Lee et al. | |
| 5,979,500 A | 11/1999 | Jahrling et al. | |
| 5,997,849 A | 12/1999 | Small et al. | |
| 5,997,891 A | 12/1999 | Fuerst et al. | |
| 6,007,797 A | 12/1999 | Bell et al. | |
| 6,038,331 A | 3/2000 | Johnson | |
| 6,086,858 A | 7/2000 | McEleney et al. | |
| 6,113,886 A | 9/2000 | Bryan | |
| 6,114,290 A | 9/2000 | Lyle et al. | |
| 6,130,435 A | 10/2000 | Rocklin | |
| 6,132,681 A | 10/2000 | Faran et al. | |
| 6,139,821 A | 10/2000 | Fuerst et al. | |
| 6,146,618 A | 11/2000 | Bell et al. | |
| 6,149,934 A | 11/2000 | Krzysik et al. | |
| 6,152,358 A | 11/2000 | Bryan | |
| 6,188,506 B1 | 2/2001 | Kaiserman et al. | |
| 6,218,189 B1 | 4/2001 | Antonoplos et al. | |
| 6,236,317 B1 | 5/2001 | Cohen et al. | |
| 6,247,995 B1 | 6/2001 | Bryan | |
| 6,248,593 B1 | 6/2001 | Esswein et al. | |
| 6,267,976 B1 | 7/2001 | Barnhart et al. | |
| 6,331,515 B1 | 12/2001 | Gambogi et al. | |
| 6,361,763 B1 | 3/2002 | Carroll | |
| 6,392,546 B1 | 5/2002 | Smith | |
| 6,419,902 B1 | 7/2002 | Wright | |
| 6,426,701 B1 | 7/2002 | Levy et al. | |
| 6,429,177 B1 | 8/2002 | Williams et al. | |
| 6,436,660 B1 | 8/2002 | Little, II | |
| 6,446,840 B2 | 9/2002 | Ophardt et al. | |
| 6,465,791 B1 | 10/2002 | Ribi et al. | |
| 6,531,118 B1 | 3/2003 | Gonzalez et al. | |
| 6,533,145 B2 | 3/2003 | Lewis et al. | |
| 6,537,335 B1 | 3/2003 | Friars et al. | |
| 6,542,568 B1 | 4/2003 | Howes, Jr. et al. | |
| 6,552,245 B1 | 4/2003 | Roessler et al. | |
| 6,569,415 B1 | 5/2003 | Orloff et al. | |
| 6,608,022 B1 * | 8/2003 | Zabarylo et al. | 510/446 |
| 6,612,846 B1 | 9/2003 | Underhill et al. | |
| 6,703,245 B2 | 3/2004 | Sumitani et al. | |
| 6,727,818 B1 | 4/2004 | Wildman et al. | |
| 6,733,766 B2 | 5/2004 | Gott et al. | |
| 6,806,213 B2 | 10/2004 | Brooks | |
| 6,814,816 B2 | 11/2004 | Achar et al. | |
| 6,830,557 B2 | 12/2004 | Paul | |
| 6,832,916 B2 | 12/2004 | Collopy | |
| 6,846,785 B2 | 1/2005 | Patel | |
| 6,882,278 B2 | 4/2005 | Winings et al. | |
| 6,896,521 B2 | 5/2005 | Underhill et al. | |
| 6,969,378 B1 | 11/2005 | Vukos et al. | |
| 7,033,614 B2 | 4/2006 | Linz et al. | |
| 7,053,029 B2 | 5/2006 | MacDonald et al. | |
| 7,776,347 B2 * | 8/2010 | Kerschner et al. | 424/401 |
| 2002/0193511 A1 * | 12/2002 | Lin | 524/806 |
| 2003/0036328 A1 | 2/2003 | De Leon et al. | |
| 2003/0044366 A1 | 3/2003 | Dole et al. | |
| 2003/0191036 A1 | 10/2003 | MacDonald et al. | |
| 2003/0202952 A1 | 10/2003 | Wells et al. | |
| 2004/0048759 A1 | 3/2004 | Ribble et al. | |
| 2005/0049157 A1 | 3/2005 | MacDonald et al. | |
| 2005/0065048 A1 | 3/2005 | MacDonald et al. | |
| 2005/0075420 A1 | 4/2005 | Stovold | |
| 2005/0090414 A1 | 4/2005 | Rich | |
| 2005/0118237 A1 | 6/2005 | Krzysik et al. | |
| 2005/0125877 A1 | 6/2005 | Benjamin et al. | |
| 2005/0134465 A1 | 6/2005 | Rice et al. | |
| 2005/0148490 A1 | 7/2005 | Krzysik et al. | |
| 2005/0191326 A1 | 9/2005 | Melker | |
| 2005/0192191 A1 | 9/2005 | Kramer et al. | |
| 2005/0239029 A1 | 10/2005 | Yzermans et al. | |
| 2005/0254551 A1 | 11/2005 | McClure et al. | |
| 2005/0256758 A1 | 11/2005 | Sierra et al. | |
| 2006/0112851 A1 * | 6/2006 | Ono et al. | 106/31.16 |
| 2006/0287215 A1 * | 12/2006 | McDonald et al. | 510/441 |
| 2007/0142263 A1 | 6/2007 | Stahl et al. | |
| 2008/0026015 A1 * | 1/2008 | MacDonald et al. | 424/401 |
| 2008/0085290 A1 * | 4/2008 | Flugge-Berendes et al. | 424/401 |
| 2008/0132438 A1 * | 6/2008 | Hoffman et al. | 510/380 |
| 2008/0259996 A1 * | 10/2008 | Lee et al. | 374/162 |
| 2008/0261843 A1 * | 10/2008 | Lee et al. | 510/146 |

FOREIGN PATENT DOCUMENTS

| | | |
|---|---|---|
| EP | 0202621 A2 | 11/1986 |
| EP | 0255978 A2 | 2/1988 |
| EP | 0255978 A3 | 2/1988 |
| EP | 0327345 A2 | 8/1989 |

| | | | |
|---|---|---|---|
| EP | 0327345 | A3 | 8/1989 |
| EP | 0418049 | A2 | 3/1991 |
| EP | 0418049 | A3 | 3/1991 |
| EP | 0471105 | | 2/1992 |
| EP | 0850039 | B1 | 7/1998 |
| EP | 0953283 | A1 | 11/1999 |
| EP | 1211512 | A2 | 6/2002 |
| FR | 2717184 | A1 | 9/1995 |
| FR | 2805162 | A1 | 8/2001 |
| GB | 1281796 | | 7/1972 |
| GB | 1313180 | | 4/1973 |
| GB | 1509450 | | 5/1978 |
| GB | 2050829 | | 1/1981 |
| GB | 2305932 | A | 4/1997 |
| JP | 01308499 | * | 12/1989 |
| WO | WO 9111171 | A1 | 8/1991 |
| WO | WO 9629047 | A1 | 9/1996 |
| WO | WO 9709957 | A1 | 3/1997 |
| WO | WO 9829487 | A1 | 7/1998 |
| WO | WO 9960089 | A1 | 11/1999 |
| WO | WO 0065911 | A1 | 11/2000 |
| WO | WO 01/12150 | A1 * | 2/2001 |
| WO | WO 0112149 | A1 | 2/2001 |
| WO | WO 0140792 | A1 | 6/2001 |
| WO | WO 0203949 | A2 | 1/2002 |
| WO | WO 0218533 | A1 | 3/2002 |
| WO | WO 0235220 | A1 | 5/2002 |
| WO | WO 03008303 3 | A2 | 10/2003 |
| WO | WO 03008303 | A3 | 10/2003 |
| WO | WO 2004026999 | A2 | 4/2004 |
| WO | WO 2004052307 | A2 | 6/2004 |
| WO | WO 2005123023 | A1 | 12/2005 |
| WO | WO 2006/137955 | A1 | 12/2006 |
| WO | WO 2007/070118 | | 6/2007 |
| WO | WO 2008/065553 | | 6/2008 |

OTHER PUBLICATIONS

Abstract of Chinese Patent No. CN1086256 May 4, 1994.
Abstract of German Patent No. DE2953574 Mar. 19, 1981.
Abstract of French Patent No. FR2673640 Sep. 11, 1992.
Abstract of Japanese Patent No. JP1308499 Dec. 13, 1989.
Abstract of Japanese Patent No. JP02957042 Sep. 17, 1993.
Abstract of Japanese Patent No. JP48047492 Jan. 7, 1978.
Abstract of Japanese Patent No. JP48070711 Sep. 25, 1973.
Abstract of Japanese Patent No. JP49076903 Jul. 24, 1974.
Abstract of Japanese Patent No. JP49081410 Aug. 6, 1974.
Abstract of Japanese Patent No. JP50103508 Aug. 15, 1975.
Abstract of Japanese Patent No. JP51020905 Feb. 19, 1976.
Abstract of Japanese Patent No. JP51020906 Feb. 19, 1976.
Abstract of Japanese Patent No. JP5239498 Sep. 17, 1993.
Abstract of Japanese Patent No. JP53058506 May 26, 1978.
Abstract of Japanese Patent No. JP61081497 Apr. 25, 1986.
Abstract of Japanese Patent No. JP61252297 Nov. 10, 1986.
Abstract of Japanese Patent No. JP61252298 Nov. 10, 1986.
Abstract of Japanese Patent No. JP61252299 Nov. 10, 1986.
Abstract of Japanese Patent No. JP63020382 Jan. 28, 1988.
Abstract of Japanese Patent No. JP73043642 Jun. 23, 1973.
Abstract of Japanese Patent No. JP75018482 Jun. 30, 1975.
Abstract of Japanese Patent No. JP2002256291 Sep. 11, 2002.
Abstract of the Netherlands Patent No. NL7211429 for FR2198991 Apr. 5, 1974.
Abstract of WO200224846 A2 Mar. 28, 2002.
Barnett, Gabriel, "Emollient Creams and Lotions," Chapter 2, *Cosmetics—Science and Technology*, Second Edition, vol. 1, John Wiley & Sons, Inc., 1972, pp. 27-104.
Boyce, John M. and Didier Pittet, "Guideline for Hand Hygiene in Health-Care Settings—Recommendations of the Healthcare Infection Control Practices Advisory Committee and the HICPAC/SHEA/APIC/IDSA Hand Hygiene Task Force," *MMMR—Morbidity and Mortality Weekly Report*, vol. 51, No. RR-16, Centers for Disease Control and Prevention, Continuing Education Examination, Oct. 25, 2002, pp. 1-48, CE-1 through CE-4.
Flick, Ernest W., "Soaps," Section XII, *Cosmetic and Toiletry Formulations*, Noyes Publications, Park Ridge, New Jersey, 1984, pp. 501-512.
Flick, Ernest W., "Soaps," Section XII, *Cosmetic and Toiletry Formulations*, Second Edition, Noyes Publications, Park Ridge, New Jersey, 1989, pp. 707-744.
Larson, Elaine L., "APIC Guideline for Handwashing and Hand Antisepsis in Health Care Settings," *AJIC Am. J. Infect. Control*, vol. 23, No. 4, Aug. 1995, pp. 251-269.
Lockhead, R.Y., "Natural and Modified Natural Polymers and Thickeners and Their Derivatives," pp. 100-113, and "Synthetic Polymers and Thickeners," pp. 113-129, *Cosmetics & Toiletries*, vol. 103, No. 12, Dec. 1988.
Strianse, S.J., "Hand Creams and Lotions," Chapter 5, *Cosmetics—Science and Technology*, Second Edition, vol. 1, John Wiley & Sons, Inc., 1972, pp. 179-222.
Article—*A Serious Look at Changeable Silly Putty*, White et al., Chem. Educator, vol. 5, No. 1, 2000, pp. 2-7.
Article—*Thermochromism in Commercial Products*, White et al., Journal of Chemical Education, vol. 76, No. 9, Sep. 1999, pp. 1201-1205.
Product Data Sheet for DynaColor™ (Thermochromic Offset Ink (Including Litho, Dry and UV Cure Offset Inks) from Chromatic Technologies, Inc., Jul. 2004, 2 pages.
Product Data Sheet for DynaColor™ (Thermochromic Water-Based Flexographic Ink) from Chromatic Technologies, Inc., Sep. 2004, 3 pages.
US 6,290,977, 09/2001, Friars et al. (withdrawn)

* cited by examiner

COLOR CHANGING CLEANSING COMPOSITION

RELATED APPLICATIONS

The present application is a continuation-in-part application and claims priority to U.S. patent application Ser. No. 11/303,009, filed on Dec. 15, 2005 now abandoned.

BACKGROUND OF THE INVENTION

One of the most effective methods found to date for limiting the spread of communicable disease is through effective personal cleaning, particularly through thorough hand washing. Thorough hand cleaning includes not only washing often with a suitable cleanser, but also washing for a period of time long enough to ensure sanitary conditions have been attained.

Many soaps and other detergent cleansers can provide the desired levels of hygiene if used correctly. However, these cleansers are usually supplied to the public in bar or liquid form, and people, particularly children, often give only a cursory wash, and therefore don't clean as thoroughly as required to remove dirt, grime and/or disease causing agents.

In order to teach children how to effectively wash their hands, parents or guardians typically rely on constant reminders and close monitoring. In fact, parents or guardians can spend a significant amount of time and attention in attempts to build and reinforce proper hygiene habits. Children, however, tend to follow the instructions only as long as they feel they are being monitored. Thus, some children grow up learning these habits only as a result of pressure from their parents or guardians, and do not maintain these habits once the pressure of close monitoring is absent.

As such, a need currently exists for a cleaning product that includes some sort of indicator for determining how long washing should continue with the product. More particularly, a need currently exists for a cleansing composition that changes color during use for indicating that sufficient time has elapsed and that washing or scrubbing with the product can discontinue. For example, a need exists for a hand soap for children and adults that teaches a user how much time should be spent washing their hands.

SUMMARY OF THE INVENTION

In general, the present disclosure is directed to an improved cleansing composition. The cleansing composition, for instance, may comprise a body wash, a facial soap, a shampoo, a baby wash, a disinfectant, a general purpose cleaner, a window cleaner, a detergent, a vehicle cleaner, pet detergent or wash or any other suitable cleaning product. For instance, in one particular embodiment, the cleansing composition may comprise a hand soap composition. In accordance with the present disclosure, the cleansing composition contains a color changing indicator that changes color based upon changes in temperature. Specifically, during use of the cleansing composition, the composition increases in temperature due to various factors. For instance, when the cleansing composition is intended to clean part of a person's body, such as a hand soap, the temperature of the composition may increase due to contact with the user, due to friction that is caused during washing, and/or due to the presence of warm water. When the cleansing product is used to clean adjacent surfaces, on the other hand, the temperature of the composition may increase due to friction that is generated during scrubbing, due to contact with a person's hand, and/or due to the presence of warm water. In accordance with the present disclosure, once the cleansing composition reaches a selected temperature, the composition can be configured to discontinue changing color indicating to the user that the user has spent sufficient time washing, wiping or scrubbing.

For example, in one embodiment, the present disclosure is directed to a cleansing composition that may be in the form of a solid or a liquid. The cleansing composition can contain, for instance, at least one surfactant and optionally an emollient, a preservative, a fragrance, and/or an anti-microbial agent In accordance with the present disclosure, a plurality of thermochromic dyes are blended with the cleansing composition in an amount sufficient to add color to the product. The thermochromic dyes are configured to change the color of the composition as the composition is heated to selected temperatures. The thermochromic dyes, for instance, may comprise leuco dyes. For example, when the cleansing composition is intended to be used to clean at least a portion of a person's body, the thermochromic dyes present in the composition may be configured to change the color of the composition as the composition is heated to temperatures of from about 21° C. to about 40° C., such as from about 23° C. to about 38° C., such as, in one embodiment, from about 25° C. to about 36° C.

When the cleansing composition is used to clean adjacent surfaces, on the other hand, the temperature at which the color change is activated may be lower or higher than the temperatures provided above.

The thermochromic dyes contained within the cleansing composition may be configured to change the color of the composition in various ways. For example, in one embodiment, once the composition reaches a selected temperature, the composition may change from a base color to a white color or a clear color. In another embodiment, a pigment or dye that does not change color based on temperature may be present in the cleansing composition for providing a base color. The thermochromic dyes, on the other hand, can be included in order to change the composition from the base color to at least one other color.

In general, the thermochromic dyes may be present in the cleansing composition in an amount from about 0.1% to about 3% by weight, such as in an amount of about 1% by weight.

In one particular embodiment, the plurality of thermochromic dyes are configured to cause the cleansing composition to change color over a temperature range of at least about 3° C., such as at least about 5° C., once the composition is heated to a selected temperature. For example, multiple thermochromic dyes may be present within the cleansing composition so that the dyes change color as the composition gradually increases in temperature. For instance, in one embodiment, a first thermochromic dye may be present that changes color at a temperature of from about 23° C. to about 28° C. and a second thermochromic dye may be present that changes color at a temperature of from about 27° C. to about 32° C. If desired, a third thermochromic dye may also be present that changes color at a temperature of from about 31° C. to about 36° C. In this manner, the cleansing composition changes color at the selected temperature and then continues to change color in a stepwise manner as the temperature of the composition continues to increase.

The plurality of thermochromic dyes may be selected so that the color change occurs over a specific amount of time based upon the predicted increase in temperature of the composition. For instance, the plurality of thermochromic dyes may be selected so that under normal use conditions, the color change occurs over a time from about 15 seconds to about 5 minutes, such as from about 15 seconds to about 45 seconds.

Once the cleansing composition stops changing color, a user then knows that they have spent an appropriate amount of time washing, scrubbing or wiping.

In order to maintain the thermochromic dyes evenly dispersed within the cleansing composition, the composition, in one embodiment, can contain a suspending agent. The suspending agent may comprise, for instance, an acrylic polymer, such as an acrylate polymer.

In other embodiments, the suspending agent may comprise a clay, a starch including starch derivatives, a modified cellulose, a natural gum, a wax, a fatty acid, a fatty alcohol, a multifunctional alcohol, colloidal or fumed particles, a fatty acid ester, a polyoxyethylene glycol ether, or mixtures thereof.

Suitable clays, for instance, that may be used as suspending agents include montmorillonite clay including bentonite clay, hectorite clay, attapulgite clay, smectite clay, saponite clay, laponite clay, and mixtures thereof. Modified celluloses that may be used in the present disclosure include ethyl cellulose, hydroxypropyl cellulose, carboxymethyl cellulose, hydroxypropyl methyl cellulose, hydroxyethyl methyl cellulose, hydroxyethyl cellulose, and the like. Natural gums that may be used as a suspending agent include guar gum, pectin, gum Arabic, locust bean gum, xanthan gum, and carrageenan gum.

When using a fatty acid as a suspending agent, the fatty acid may have from about 8 to about 22 carbon atoms in the carbon chain. Fatty acid suspending agents also include polyvalent metals salts thereof. Particular examples of fatty acid suspending agents include decanoic acid, lauric acid, dodecanoic acid, palmitic acid, myristic acid, stearic acid, oleic acid, eicosanoic acid, tallow fatty acid, coco fatty acid, and soya fatty acid.

Fatty alcohols that may be used as suspending agents includes fatty alcohols having the follow formula $RCH_2OH$, wherein R is an alkyl group having from about 7 to 19 carbon atoms.

Multifunctional alcohols well suited for use as suspending agents in the present disclosure include unmodified polyoxyethylene glycol polymers (PEG polymers). More particularly, suspending agents that may be used in accordance with the present disclosure include PEG polymers that are solid at a temperature of 70° F. Examples of multifunctional alcohols include, for instance, PEG-16, PEG-18, PEG-20, PEG-32, PEG-40, and the like as long as the polyoxyethylene glycol polymer is solid at 70° F.

Fatty acid esters that may be used as suspending agents include polyhydroxy esters, such as glyceryl stearate and glycol stearate, and glycol diesters, such as glycol distearate.

Other suspending agents may also include polyoxyethylene glycol fatty acid esters and polyoxyethylene glycol ethers. Polyoxyethylene glycol fatty acid esters and polyoxyethylene glycol ethers that may be used as suspending agents include polyoxyethylene glycol stearate, polyoxyethylene glycol distearate, polyoxyethylene glycol diisostearate, polyoxyethylene glycol pentaerythrityl tetrastearate, methyl glucose dioleate, polyoxyethylene glycol methyl glucose distearate, polyoxyethylene glycol methyl glucose laureate, polyoxyethylene glycol methyl glucose sesquistearate, and mixtures thereof.

As described above colloidal or fumed particles may also be used as suspending agents. In one embodiment, the colloidal or fumed particles comprise silica. The silica particles can have a particle size of less than about 2 microns, such as less than about 1 micron.

The suspending agent may be present in the cleansing composition in an amount sufficient to prevent the thermochromic dyes from settling. The suspending agent may be present in the composition in an amount from about 0.1 percent to about 15 percent by weight, such as from about 0.1 to about 10 percent by weight. In one embodiment, a laponite clay is present as a suspending agent in an amount from about 0.5 percent to about 3 percent by weight.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

According to the Center for Disease Control, which is a division of the U.S. Department of Health and Human Services, proper hand washing can be one of the most effective steps that can be taken to prevent the spread of diseases and infections. Proper hand washing according to various sources requires not only using soap but also washing for a sufficiently long period of time in order to remove dirt and any microorganisms that may be present on the skin. For example, the Center for Disease Control has stated that hand washing should last at least 15 seconds. Further, for routine hand washing, the hands should be rubbed together vigorously in the presence of a soap lather, followed by thorough rinsing under a stream of water. Soap containing anti-microbial agents are also recommended.

Adults and children alike, however, tend to hurry through the task of hand washing and typically do not use soap, do not use a sufficient amount of soap, or do not rub a soap product over their hands for a sufficient length of time necessary to remove substantially all microorganisms that may be present.

Children in particular are known not to appreciate the importance of hand washing or simply dislike the task of hand washing even though children continue to play in environments where microorganisms are freely transferred. Parents and other adults attempt to remind children continuously of the need to properly wash their hands. Even with constant reminders, however, children continue to not wash their hands properly unless an adult is actually present during the task. Adult supervision, however, is not often practical during every hand washing episode.

In this regard, the present disclosure, in one embodiment, is generally directed to a personal cleansing composition such as a hand soap composition that is intended to change color as the composition is used in order to indicate to a user when a presumably sufficient time of washing has passed. By changing color as will be described in more detail below, the hand soap composition also educates children and adults about proper hand washing procedures. The visual stimuli not only reinforces proper hygiene habits, but is believed to also encourage children and adults to properly wash their hands.

The hand soap composition of the present disclosure can also be formulated and used in more specific hand scrubbing processes. For example, the hand soap composition of the present disclosure may also be specifically formulated as a surgical or medical hand soap where hand scrubbing is to continue for longer periods of time, such as for periods of time greater than about two minutes, such as from about four minutes to about six minutes.

Although the teachings of the present disclosure are particularly well suited to formulating hand soap compositions, it should be understood that various other cleansing compositions may be made in accordance with the present disclosure. For instance, other cleansing compositions that may be made in accordance with the present disclosure include shampoos, facial soaps, body washes, baby washes, and pet detergents or washes. Further, other cleansing compositions can also be formulated that may not be intended to wash part of a person's body. For instance, other cleansing compositions that may be made in accordance with the present disclosure include disinfectants, general purpose cleaners, window cleaners, detergents, vehicle cleaners, or any other suitable cleaning products.

In accordance with the present disclosure, the cleansing composition contains a plurality of thermochromic dyes that cause the cleansing composition to change color as the composition is heated during use. In general, any suitable thermochromic dye may be used in accordance with the present disclosure. Thermochromic dyes are temperature sensitive dyes that temporarily or permanently change color when exposed to heat.

Thermochromic dyes come in various forms. For instance, in one embodiment, the thermochromic dye may comprise a leuco dye. In an alternative embodiment, the thermochromic dye may comprise liquid crystals. Most thermochromic dyes undergo a color change from a specific color to colorless (i.e. clear) once heated to a certain temperature.

In accordance with the present disclosure, the cleansing composition contains a plurality of thermochromic dyes so that the cleansing composition changes color for a long enough period of time to ensure proper washing, scrubbing or wiping. The present inventors have discovered that using a single thermochromic dye does not produce an acceptable product for most applications. For instance, thermochromic dyes change color at a specific temperature. If a single thermochromic dye is used that changes color at a relatively lower temperature, the color change may occur too rapidly and quickly to serve as an indicator that washing is complete. Incorporating a single thermochromic dye that changes color at a relatively higher temperature, on the other hand, takes too long for any color change to occur.

By incorporating a plurality of thermochromic dyes into the cleansing composition, the composition can change color quickly after use and can continue to change color at successive temperatures for an overall period of time sufficient to indicate to the user that washing, scrubbing or wiping is complete. For example, in one embodiment, the cleansing composition contains at least two thermochromic dyes, and, in other embodiments, at least three or four thermochromic dyes.

In one embodiment, the thermochromic dyes can be selected to cause the cleansing composition to initially change color as soon as the composition is being used. For example, when formulating a hand soap composition, the composition can be configured to change color as soon as the composition is applied to the hands and the hands are rubbed together. As the composition increases in temperature, further thermochromic dyes present in the composition continue to cause color change.

During use, the cleansing composition may increase in temperature due to various factors. For example, when the cleansing composition is formulated as a hand soap composition, the hand soap composition may be at ambient temperature initially. Ambient temperature or room temperature, for example, can be from about 18° C. to about 22° C. Once dispensed upon the hands of a user, the hand soap composition begins to increase in temperature due to the user's body temperature and due to the motion of rubbing both hands together. In addition, the hand soap composition may be contacted with warm water that is being dispensed from an adjacent faucet. Thus, depending upon the above factors, the hand soap composition may increase in temperature during use to temperatures up to about 37° C. or even greater. Other personal cleansing compositions can experience approximately the same temperature increases as described above, especially when the personal cleansing composition is used to wash or cleanse a part of a person's body.

In accordance with the present disclosure, a plurality of thermochromic dyes may be present in the cleansing composition that cause a color change to occur over a temperature range of at least about 3° C., such as at least about 4° C., such as at least about 5° C., such as at least about 6° C. during washing. For instance, the color change can occur over a temperature range of from about 3° C. to about 20° C., such as from about 5° C. to about 10° C. The color change can be gradual as the cleansing composition increases in temperature or the color change may occur in a stepwise manner. For example, the color change may occur at every 2° C. increase in temperature, such as at every 3° C. increase in temperature, or at every 4° C. increase in temperature. Further, the color change may comprise a change from a certain color to a clear color, from one color to another color, or from one shade of a color to a lighter or darker shade.

The particular thermochromic dyes that are combined together and used in the cleansing composition can be selected based upon the particular application and the desired results. In one embodiment, for instance, a first thermochromic dye may be present in the cleansing composition that causes an initial color change to occur at a temperature slightly above room temperature. For instance, the first color change can occur at a temperature of from about 23° C. to about 30° C., such as from about 25° C. to about 28° C. A second thermochromic dye may be present that causes a color change to occur at a temperature greater than the temperature at which the first thermochromic dye changes color. For example, the second thermochromic dye may change color at a temperature of from about 27° C. to about 35° C., such as from about 29° C. to about 32° C.

If desired, a third thermochromic dye may also be present in the cleansing composition that changes color at a temperature greater than the first and second thermochromic dyes. For instance, if present, the third thermochromic dye may change color at a temperature of from about 31° C. to about 37° C., such as from about 34° C. to about 36° C. It should be understood, however, that more thermochromic dyes may be present if desired. For instance, the cleansing composition may contain a thermochromic dye that causes a color change to occur at every 1° C. to 4° C. increase in temperature.

It should be understood, that the above temperature ranges are for exemplary purposes only. For instance, the above temperature ranges may be well suited to formulating a hand soap composition. When formulating a cleansing composition used to clean adjacent surfaces or objects, however, the composition may not increase in temperature to the extent as described above. Such cleansing compositions may include, for instance, disinfectants, general purpose cleaners, window cleaners, vehicle cleaners, and other similar cleaning products. For these products, the thermochromic dyes may be incorporated into the cleansing composition so that the cleansing composition initially changes color at a relatively low temperature when the composition is used to clean, for instance, countertops, windows, and other similar objects. In still other embodiments, it may be desirable to have the initial color change occur at relatively high temperatures. For instance, if a particular cleaning product is to be used with warm water at a particular temperature, it may be preferred to have the initial color change occur at a temperature higher than the temperature of the water that is to be mixed with the product. With these considerations in mind, cleansing compositions made in accordance with the present disclosure that are intended to clean adjacent surfaces or objects may initially undergo a color change at a temperature of from about 15° C. to about 45° C., such as from about 21° C. to about 40° C.

When incorporating multiple thermochromic dyes into a cleansing composition to be used to clean adjacent surfaces and objects, the temperature increase during use of the product may be relatively small. For instance, the increase in temperature during use of the product may be less than about 8° C., such as less than about 5° C. Thus, the thermochromic dyes incorporated into the product may be configured to cause a color change to occur at every 1° C. to about 2° C. increase in temperature.

When the cleansing composition is intended to be used to clean a portion of a person's body, the plurality of thermochromic dyes present in the composition may be selected so that a color change occurs for a certain length of time after washing is initiated. For instance, if the cleansing composition is a hand soap, thermochromic dyes may be present in the composition so as to cause the composition to change color for at least about 10 seconds, such as for at least about 15 seconds, such as at least about 20 seconds. For example, depending upon the particular hand soap formulation, one can predict how much the formulation will increase in temperature during use. Based upon the temperature increase over a desired length of time, one can then specifically formulate a plurality of thermochromic dyes sufficient to cause the color change to occur over the desired period of time.

As will be described in greater detail below, the thermochromic dyes can be incorporated into any suitable cleansing composition in accordance with the present disclosure. The cleansing composition, for instance, may be in a liquid form or in a solid form. When in a liquid form, the cleansing composition may have a relatively high viscosity or relatively low viscosity. The mixture of thermochromic dyes can also be incorporated into a cleansing composition that is intended to be aerated and form a foam such as a foam mousse as it is dispensed. As described above, each of these products may increase in temperature at a different rate during a typical washing exercise. The mixture of thermochromic dyes can be incorporated into the particular product and designed to provide a suitable indication when a sufficient period of time has passed to indicate that washing, scrubbing or wiping is complete.

Any thermochromic substance that undergoes a color change at the desired temperature may generally be employed in the present disclosure. For example, liquid crystals may be employed as a thermochromic substance in some embodiments. The wavelength of light ("color") reflected by liquid crystals depends in part on the pitch of the helical structure of the liquid crystal molecules. Because the length of this pitch varies with temperature, the color of the liquid crystals is also a function of temperature. One particular type of liquid crystal that may be used in the present disclosure is a liquid crystal cholesterol derivative. Exemplary liquid crystal cholesterol derivatives may include alkanoic and aralkanoic acid esters of cholesterol, alkyl esters of cholesterol carbonate, cholesterol chloride, cholesterol bromide, cholesterol acetate, cholesterol oleate, cholesterol caprylate, cholesterol oleyl-carbonate, and so forth. Other suitable liquid crystal cholesterol derivatives are described in U.S. Pat. Nos. 3,600,060 to Churchill, et al.; U.S. Pat. No. 3,619,254 to Davis; and U.S. Pat. No. 4,022,706 to Davis, which are incorporated herein in their entirety by reference thereto for all purposes.

In addition to liquid crystals, another suitable thermochromic substance that may be employed in the present disclosure is a composition that includes a proton accepting chromogen ("Lewis base") and a solvent. The melting point of the solvent controls the temperature at which the chromogen will change color. More specifically, at a temperature below the melting point of the solvent, the chromogen generally possesses a first color (e.g., red). When the solvent is heated to its melting temperature, the chromogen may become protonated or deprotonated, thereby resulting in a shift of the absorption maxima. The nature of the color change depends on a variety of factors, including the type of proton-accepting chromogen utilized and the presence of any additional temperature-insensitive chromogens. Regardless, the color change is typically reversible.

Although not required, the proton-accepting chromogen is typically an organic dye, such as a leuco dye. In solution, the protonated form of the leuco dye predominates at acidic pH levels (e.g., pH of about 4 or less). When the solution is made more alkaline through deprotonation, however, a color change occurs. Of course, the position of this equilibrium may be shifted with temperature when other components are present. Suitable leuco dyes for use in the present disclosure may include, for instance, phthalides; phthalanes; substituted phthalides or phthalanes, such as triphenylmethane phthalides, triphenylmethanes, or diphenylmethanes; acyl-leucomethylene blue compounds; fluoranes; indolylphthalides, spiropyranes; cumarins; and so forth. Exemplary fluoranes include, for instance, 3,3'-dimethoxyfluorane, 3,6-dimethoxyfluorane, 3,6-di-butoxyfluorane, 3-chloro-6-phenylamino-flourane, 3-diethylamino-6-dimethylfluorane, 3-diethylamino-6-methyl-7-chlorofluorane, and 3-diethyl-7,8-benzofluorane, 3,3'-bis-(p-dimethyl-aminophenyl)-7-phenylaminofluorane, 3-diethylamino-6-methyl-7-phenylamino-fluorane, 3-diethylamino-7-phenyl-aminofluorane, and 2-anilino-3-methyl-6-diethylamino-fluorane. Likewise, exemplary phthalides include 3,3',3"-tris(p-dimethylaminophenyl)phthalide, 3,3'-bis(p-dimethyl-aminophenyl)phthalide, 3,3-bis(p-diethylamino-phenyl)-6-dimethylamino-phthalide, 3-(4-diethylaminophenyl)-3-(1-ethyl-2-methylindol-3-yl)phthalide, and 3-(4-diethylamino-2-methyl)phenyl-3-(1,2-dimethylindol-3-yl)phthalide.

Although any solvent for the thermochromic dye may generally be employed in the present disclosure, it is typically desired that the solvent have a low volatility. For example, the solvent may have a boiling point of about 150° C. or higher, and in some embodiments, from about 170° C. to about 280° C. Likewise, the melting temperature of the solvent is also typically from about 25° C. to about 40° C., and in some embodiments, from about 30° C. to about 37° C. Examples of suitable solvents may include saturated or unsaturated alcohols containing about 6 to 30 carbon atoms, such as octyl alcohol, dodecyl alcohol, lauryl alcohol, cetyl alcohol, myristyl alcohol, stearyl alcohol, behenyl alcohol, geraniol, etc.; esters of saturated or unsaturated alcohols containing about 6 to 30 carbon atoms, such as butyl stearate, methyl stearate, lauryl laurate, lauryl stearate, stearyl laurate, methyl myristate, decyl myristate, lauryl myristate, butyl stearate, lauryl palmitate, decyl palmitate, palmitic acid glyceride, etc.; azomethines, such as benzylideneaniline, benzylidenelaurylamide, o-methoxybenzylidene laurylamine, benzylidene p-toluidine, p-cumylbenzylidene, etc.; amides, such as acetamide, stearamide, etc.; and so forth.

The thermochromic composition may also include a proton-donating agent (also referred to as a "color developer") to facilitate the reversibility of the color change. Such proton-donating agents may include, for instance, phenols, azoles, organic acids, esters of organic acids, and salts of organic acids. Exemplary phenols may include phenylphenol, bisphenol A, cresol, resorcinol, chlorolucinol, b-naphthol, 1,5-dihydroxynaphthalene, pyrocatechol, pyrogallol, trimer of p-chlorophenol-formaldehyde condensate, etc. Exemplary azoles may include benzotriaoles, such as 5-chlorobenzotriazole, 4-laurylaminosulfobenzotriazole, 5-butylbenzotriazole, dibenzotriazole, 2-oxybenzotriazole, 5-ethoxycarbonylbenzotriazole, etc.; imidazoles, such as oxybenzimidazole, etc.; tetrazoles; and so forth. Exemplary organic acids may include aromatic carboxylic acids, such as salicylic acid, methylenebissalicylic acid, resorcylic acid, gallic acid, benzoic acid, p-oxybenzoic acid, pyromellitic acid, b-naphthoic acid, tannic acid, toluic acid, trimellitic acid, phthalic acid, terephthalic acid, anthranilic acid, etc.; aliphatic carboxylic acids, such as stearic acid, 1,2-hydroxystearic acid, tartaric acid, citric acid, oxalic acid, lauric acid, etc.; and so forth. Exemplary esters may include alkyl esters of aromatic carboxylic acids in which the alkyl moiety has 1 to 6 carbon atoms, such as butyl gallate, ethyl p-hydroxybenzoate, methyl salicylate, etc.

The amount of the proton-accepting chromogen employed may generally vary, but is typically from about 2 wt. % to about 20 wt. %, and in some embodiments, from about 5 to about 15 wt. % of the thermochromic substance. Likewise, the proton-donating agent may constitute from about 5 to about 40 wt. %, and in some embodiments, from about 10 wt. % to about 30 wt. % of the thermochromic substance. In addition, the solvent may constitute from about 50 wt. % to about 95 wt. %, and in some embodiments, from about 65 wt. % to about 85 wt. % of the thermochromic composition.

Regardless of the particular thermochromic substance employed, it may be microencapsulated to enhance the stability of the substance during processing. For example, the thermochromic substance may be mixed with a thermosetting resin according to any conventional method, such as interfacial polymerization, in-situ polymerization, etc. The thermosetting resin may include, for example, polyester resins, polyurethane resins, melamine resins, epoxy resins, diallyl phthalate resins, vinylester resins, and so forth. The resulting mixture may then be granulated and optionally coated with a hydrophilic macromolecular compound, such as alginic acid and salts thereof, carrageenan, pectin, gelatin and the like, semisynthetic macromolecular compounds such as methylcellulose, cationized starch, carboxymethylcellulose, carboxymethylated starch, vinyl polymers (e.g., polyvinyl alcohol), polyvinylpyrrolidone, polyacrylic acid, polyacrylamide, maleic acid copolymers, and so forth. The resulting thermochromic microcapsules typically have a size of from about 1 to about 50 micrometers, and in some embodiments, from about 3 to about 15 micrometers. Various other microencapsulation techniques may also be described in U.S. Pat. Nos. 4,957,949 to Kamada, et al. and U.S. Pat. No. 5,431,697 to Kamata, et al., which are incorporated herein in their entirety by reference thereto for all purposes. Suitable microencapsulated thermochromic substances may also be obtained from Matsui Shikiso Chemical Co., Ltd. of Kyoto, Japan under the designation "Chromicolor."

Thermochromic dyes are commercially available from various sources. In one embodiment, for instance, thermochromic dyes marketed by Chromatic Technologies, Inc. of Ithaca, N.Y. may be incorporated into the cleansing composition.

The thermochromic dyes can be present in the cleansing composition in an amount sufficient to have a visual effect on the color of the composition. The amount or concentration of the dyes can also be increased or decreased depending upon the desired intensity of any color. In general, the thermochromic dyes may be present in the cleansing composition in an amount from about 0.01% by weight to about 9% by weight, such as from about 0.1% by weight to about 3% by weight. For instance, in one particular embodiment, the thermochromic dyes may be present in an amount from about 0.3% to about 1.5% by weight.

As described above, thermochromic dyes typically change from a specific color to clear at a certain temperature. If desired, other pigments or dyes can be added to the cleansing composition in order to provide a background color that remains constant independent of the temperature of the composition. By adding other pigments or dyes in combination with the thermochromic dyes to the cleansing composition, the thermochromic dyes can provide a color change at certain temperatures rather than just a loss of color should the thermochromic dye become clear. For instance, a non-thermochromic pigment, such as a yellow pigment, may be used in conjunction with a plurality of thermochromic dyes, such as a red dye and a blue dye. When all combined together, the cleansing composition may have a dark color. As the composition is increased in temperature, the red thermochromic dye may turn clear changing the color to a green shade (a combination of yellow and blue). As the temperature further increases, the blue thermochromic dye turns clear causing the cleansing composition to turn yellow indicating to a user that a sufficient amount of washing has occurred.

It should be understood, that all different sorts of thermochromic dyes and non-thermochromic pigments and dyes may be combined in order to produce a cleansing composition having a desired base color and one that undergoes desired color changes. The color changes, for instance, can be somewhat dramatic and fanciful. For instance, in one embodiment, the cleansing composition may change from green to yellow to red, such as the colors of a stop light, during a washing operation. Once the color of the composition turns red, a user would understand that sufficient time has elapsed and that the washing process is complete.

In an alternative embodiment, however, the composition can contain different thermochromic dyes all having the same color. As the temperature of the composition is increased, however, the shade or intensity of the color can change. For instance, the composition can change from a vibrant blue to a light blue to a clear color during normal washing.

In addition to the above, it should be understood that many alterations and permutations are possible. Any of a variety of colors and shades can be mixed in order to undergo color changes as a function of temperature.

When thermochromic dyes are used in conjunction with non-thermochromic pigments or dyes, the non-thermochromic pigments or dyes may comprise any suitable pigments or dyes that do not interfere with the cleansing composition or with the function of the thermochromic dyes.

In one embodiment, in order to maintain the thermochromic dyes dispersed throughout the cleansing composition, the thermochromic dyes may be added to the cleansing composition in the presence of a suspending agent. The suspending agent can ensure that the thermochromic dyes do not agglomerate or otherwise settle out of solution. In one embodiment, for instance, the suspending agent may comprise an acrylic polymer, such as an acrylate, that is designed to suspend the dyes and to stabilize and/or thicken the cleansing composition. For instance, in one embodiment, the suspending agent may comprise CARBOPOL AQUA SF-1 polymer available from Noveon, Inc. of Cleveland, Ohio. CARBOPOL AQUA SF-1 polymer is a lightly cross-linked acrylic polymer dispersion that has carboxyl functionality in its protonated form. The suspending agent may be present in the cleansing composition in an amount from about 0.5% by weight to about 15% by weight, such as from about 1% by weight to about 10% by weight.

In other embodiments, non-acrylic based suspending agents may be used. For instance, the suspending agent may comprise a clay, a starch, a cellulose, a gum, a fatty acid, a fatty alcohol, a multifunctional alcohol, colloidal or fumed particles, or other non-acrylic based water soluble polymeric thickeners. The suspending agents can be added in an amount sufficient to suspend the dyes and to otherwise stabilize the composition.

For instance, in one embodiment, clay particles may be added to the cleansing composition as the suspending agent. The clay particles may comprise, for instance, any suitable phyllosilicate material. The clay particles, for instance, can generally have a particle size of less than about 2 microns. Clays that are particularly well suited for use in the present disclosure include colloid forming clays that are either natural clays or synthetic clays. Particular examples of clays that may be used include laponite, montmorillonite including bentonite clays, hectorite clays, attapulgite clays, smectite clays, saponite clays, mixtures thereof, and the like.

In one particular embodiment, the suspending agent may comprise laponite clay, such as Laponite XLG commercially available from Southern Clay Products. Laponite XLG is a synthetic, layered clay, similar to natural smectites.

In another embodiment, the suspending agent may comprise a starch, which includes starch derivates. Starches are generally available from plants, such as corn, rice or tapioca and comprise a complex carbohydrate. Starch derivatives generally include starches that have been hydrolyzed into simpler carbohydrates by acids, enzymes, or a combination of the two.

Another example of a suspending agent that may be used in the present disclosure includes cellulose materials, particularly modified cellulose. Modified cellulose is generally referred to cellulose where the hydroxyl groups of the cellulose are partially or fully reacted with various chemicals. Modified celluloses include cellulose esters and cellulose ethers. Cellulose suspending agents particularly well suited for use in the present disclosure include ethyl cellulose, hydroxypropyl cellulose, carboxymethyl cellulose, hydroxypropyl methyl cellulose, hydroxyethyl methyl cellulose, hydroxyethyl cellulose, and combinations thereof.

In still another embodiment, the suspending agent may comprise a natural gum. Natural gums well suited for use in the present disclosure include guar gum, carrageenan, gum Arabic, locust bean gum, xanthan gum, and mixtures thereof. Natural gums also include any derivatives of the above gums. For instance, hydroxypropyl guar gum may also be used.

Another class of suspending agents that may be used in the present disclosure include fatty acids and fatty acid alcohols. Fatty acids that may be used, for instance, include aliphatic fatty carboxylic acids having from about 8 carbon atoms to about 22 carbon atoms in the carbon chain, such as from about 10 carbon atoms to about 20 carbon atoms in the carbon chain. The aliphatic radical may be saturated or unsaturated and may be straight or branched. Mixtures of fatty acids may also be used such as those derived from natural sources such as tallow fatty acid, coco fatty acid, soya fatty acid, and the like. Synthetically available fatty acids may also be used.

Particular examples of fatty acids which can be used include decanoic acid, lauric acid, dodecanoic acid, palmitic acid, myristic acid, stearic acid, oleic acid, eicosanoic acid, tallow fatty acid, coco fatty acid, soya fatty acid, and mixtures thereof.

As used herein, fatty acids include the polyvalent metal salts of the above fatty acids. Polyvalent metals that may be used to form the salts include, for instance, magnesium, calcium, aluminum, and zinc.

Fatty alcohols that may be used as a suspending agent include alcohols of any of the above described fatty acids. In one particular embodiment, for instance, the fatty alcohol may have the following formula:

$RCH_2OH$ wherein R is an alkyl group having from about 7 carbon atoms to about 19 carbon atoms, such as from about 9 carbon atoms to about 17 carbon atoms. Fatty alcohols also include those fatty alcohols that have been alkoxylated. For instance, a fatty alcohol containing from about 6 to about 22 carbon atoms in the carbon chain can be alkoxylated with ethylene oxide. The ethylene oxide may be present in an amount from about 5 moles to about 90 moles.

Particular examples of fatty alcohols that may be used include tauryl alcohol, oleyl alcohol, stearyl alcohol, cetyl alcohol, and the like.

Multifunctional alcohols may also be used as suspending agents in accordance with the present disclosure. For instance, multifunctional alcohols may include unmodified polyoxyethylene glycol polymers that are solid at 70° F. Polyoxyethylene glycol polymers that may be used include, for example, PEG-16, PEG-18, PEG-20, PEG-32, PEG-40, and the like.

In still another embodiment, the suspending agent may comprise a fatty acid ester or a polyoxyethylene glycol ether. For example, the suspending agent may comprise a polyoxyethylene glycol fatty acid of glycerol or a polyoxyethylene glycol ether of a diester of methyl glucose and a fatty acid. Particular examples include PEG-150 distearate, PEG-150 diisostearate, PEG-150 pentaerythrityl tetrastearate, PEG-120 methyl glucose trioleate, PEG-20 glyceryl oleate, PEG-120 methyl glucose dioleate, PEG-20 methyl glucose distearate, PEG-80 methyl glucose laureate, PEG-20 methyl glucose sesquistearate, and mixtures thereof.

Other fatty acid esters that may be used as suspending agents include polyhydroxy esters, such as glyceryl stearate and glycol stearate. Other fatty acid esters include glycol diesters, such as glycol distearate.

The amount of suspending agents contained in the cleansing composition can depend upon numerous factors. In general the one or more suspending agents may be present in the cleansing composition in an amount from about 0.1 to about 15 percent by weight, such as from about 0.1 to about 10 percent by weight, such as from about 0.5 percent to about 5 percent by weight.

As stated above, the plurality of thermochromic dyes may be combined with any suitable cleansing composition in accordance with the present disclosure. The cleansing composition can contain numerous different ingredients depending upon various factors, including the desired use of the product.

For many applications, the cleansing composition can contain one or more surfactants and/or one or more emollients, especially when the cleansing composition is used to clean part of a person's body, although surfactants are also used in numerous cleansing compositions designed to clean adjacent surfaces or objects. The surfactants and/or emollients can be contained in a carrier, such as water or an alcohol. In addition, the cleansing composition can contain sequestrants, non-aqueous solvents, preservatives, pH modifiers, anti-microbial agents, disinfectants and various other optional ingredients.

For exemplary purposes only, the following is a list of possible components that can be contained in the cleansing composition.

Surfactants

As described above, the cleansing composition can contain one or more surfactants. A surfactant can also serve as an emollient.

Nonionic, anionic, cationic, and amphoteric surfactants, such as zwitterionic surfactants, may all be suitable for use in the present disclosure. Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof.

Various specific examples of suitable nonionic surfactants include, but are not limited to, methyl gluceth-10, PEG-20 methyl glucose distearate, PEG-20 methyl glucose sesquistearate, C11-C15 pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty (C6-C22) alcohol, including 3 to 20 ethylene oxide moieties, polyoxyethylene-20 isohexadecyl ether, polyoxyethylene-23 glycerol laurate, PEG-80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG-600 dioleate, PEG-400 dioleate, and mixtures thereof.

Additional nonionic surfactants that can be used include water soluble alcohol ethylene oxide condensates, such as the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol® from Union Carbide Corp., Danbury, Conn. Specific examples of such commercially available nonionic surfactants of the foregoing type are C11-C15 secondary alkanols condensed with either 9 moles of ethylene oxide (Tergitol® 15-S-9) or 12 moles of ethylene oxide (Tergitol® 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal® CO-630 (a nonyl phenol ethoxylate) marketed by ISP Corp. (Wayne, N.J.). Suitable non-ionic ethoxylated octyl and nonyl phenols include those having from about 7 to about 13 ethoxy units. Such compounds are commercially available under the trade name Triton® X (Union Carbide, Danbury, Conn.).

Alkyl polyglycosides may also be used as a nonionic surfactant in the present inventive compositions. Suitable alkyl polyglycosides are known nonionic surfactants that are alkaline and electrolyte stable. Alkyl mono and polyglycosides are prepared generally by reacting a monosaccharide, or a compound hydrolyzable to a monosaccharide with an alcohol such as a fatty alcohol in an acid medium.

One example of such alkyl polyglycosides is APG™ 325 CS GLYCOSIDE, which is described as being a 50% C9-C11 alkyl polyglycoside, also commonly referred to as D-glucopyranoside. Another example of an alkyl polyglycoside surfactant is GLUCOPON™ 625 CS, which is described as being a 50% C10-C16 alkyl polyglycoside, also commonly referred to as a D-glucopyranoside. Both APG™ 325 CS GLYCOSIDE and GLUCOPON™ 625 CS are commercially available from Henkel Corp., Ambler, Pa.

Other useful nonionic surfactants include compositions based on amine oxides. One general class of useful amine oxides include alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide.

Another class of useful amine oxides include alkyl di(hydroxy lower alkyl) amine oxides in which the alkyl group has about 10-20, and particularly 12-16 carbon atoms, and can be straight or branched chain, saturated or unsaturated. Examples are bis(2-hydroxyethyl) cocoamine oxide, bis(2-hydroxyethyl) tallow amine oxide, and bis(2-hydroxyethyl) stearylamine oxide. Moreover, still other useful amine oxides include those characterized as alkylamidopropyl di(lower alkyl) amine oxides, in which the alkyl group has about 10-20 carbon atoms, and can be straight or branched chain, saturated or unsaturated. Examples are cocoamidopropyl dimethyl amine oxide and tallowamidopropyl dimethyl amine oxide.

Additional useful amine oxides include alkylmorpholine oxides in which the alkyl group has about 10-20 carbon atoms, and can be straight or branched chain, saturated or unsaturated. Further examples of amine oxides include those that commercially under the trade name AMMONYX (Stepan Co., Chicago, Ill.).

In addition to nonionic surfactants, the cleansing composition may also contain other types of surfactants. For instance, in some embodiments, amphoteric surfactants, such as zwitterionic surfactants, may also be used. For instance, one class of amphoteric surfactants that may be used in the present disclosure are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

Additional classes of suitable amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, cocamidopropyl betaine, lauric myristic amido propyl monosodium phosphitaine, and mixtures thereof.

In certain instances, it may also be desired to utilize one or more anionic surfactants within the cleansing composition. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Cationic surfactants, such as cetylpyridinium chloride and methylbenzethonium chloride, may also be utilized.

The amount of surfactant contained in the cleansing composition can vary greatly depending upon various factors. In some embodiments, the cleansing composition can contain surfactants in an amount from about 1% to about 60% by weight, such as from about 5% to about 40% by weight.

Emollients

The cleansing composition can also contain various emollients. In fact, some of the above described surfactants may be considered emollients. Particular emollients that may be used include ethoxylated and propoxylated alcohols, such as cetyl alcohols and ethoxylated lanolin.

Non-Aqueous Solvents

In some instances, the cleansing composition may also include one or more non-aqueous solvents. Although not required, non-aqueous solvents can sometimes aid in dissolving certain components (e.g., preservatives, anti-microbial agent, etc.). Examples of some suitable non-aqueous solvents include, but are not limited to, glycerine; glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Solvent combinations include a glycol, particularly hexylene and/or propylene glycol, and one or more lower alcohols, particularly isopropanol, n-propanol, and/or ethanol.

Preservatives

The cleansing composition can also contain various preservatives to increase the shelf life of the composition.

Some suitable preservatives that can be used in the present disclosure include, but are not limited to, Kathon CG®, which is a mixture of methylchloroisothiazolinone and methylisothiazolinone available from Rohm & Haas; Mackstat H 66 (available from Mcintyre Group, Chicago, Ill.); DMDM hydantoin (e.g., Glydant Plus, Lonza, Inc., Fair Lawn, N.J.); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

When utilized, the amount of the preservative utilized in the cleansing composition can generally vary depending on the relative amounts of the other components present within the formulation. For example, in some embodiments, the preservative is present in the formulation in an amount between about 0.001% to about 5% by weight, in some embodiments between about 0.001 to about 1% by weight, and in some embodiments, between about 0.1% to about 0.15% by weight of the disinfectant formulation.

pH Modifiers

In general, the pH of the cleansing composition may be controlled to be within any desired range.

If necessary, various pH modifiers may be utilized in the cleansing composition to achieve the desired pH level. For instance, some examples of basic pH modifiers that may be used in the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the present disclosure include, but are not limited to, mineral acids; and carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, and alginic acid.

Sequestrants

In one embodiment, the cleansing composition may contain one or more sequestrants. A sequestrant is a substance whose molecules can form one or more bonds with a metal ion. In particular, water often contains metal ions, such as calcium ions, that might react with anionic components (e.g., surfactants, acids, etc.) present within the composition. For example, in one embodiment, a surfactant that remains substantially unreacted with metal ions can better function as a cleansing agent.

Some examples of sequestrants that may be used in the cleansing composition of the present disclosure include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

Carrier

For many applications, the cleansing composition may contain a carrier for the various components. For instance, water and/or an alcohol may be used as a carrier. When present, water can be included in an amount sufficient to control the viscosity of the composition. In this regard, water can be present in an amount from about 1% to about 99% by weight, such as from about 40% to about 99% by weight.

For example, the amount of water added to the composition can be controlled so as to produce a cleansing composition that has a relatively high viscosity or relatively low viscosity. Cleansing compositions that are intended to foam when dispensed, for instance, typically have a relatively low viscosity.

Other Optional Ingredients

In order to better enhance the composition, other optional ingredients can also be used. For instance, some classes of ingredients that can be used include, but are not limited to: anti-microbial agents, antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some anti-microbial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens and thickeners (to increase the viscosity of the formulation).

As described above, the cleansing composition of the present disclosure may be produced in liquid form or in a solid form, which can impact the type of ingredients that are present in the composition. In one embodiment, the thermochromic dyes can be incorporated into a solid cleansing composition intended to be used to clean the hands, the face, and/or the body of a user. In one embodiment, the thermochromic dyes may be incorporated into an alkali soap in the form of a soap bar. Alkali soaps are well known in the art. Such soaps are typically formed from an acid-base composition. The soaps, for instance, can contain an acid, such as a fatty acid that is neutralized with a base. The acid may comprise, for instance, tallow which comprises primarily triglycerides of stearic, palmitic, and oleic acids. The tallow can be combined with, for instance, lye in order to form the soap.

The thermochromic dyes can also be incorporated into solid cleansers made from synthetic materials. Such cleansers can be made from, for instance, a flaked surfactant such as sodium cocoyl isethionate. These cleansers can also contain various fillers, such as dextrin.

In still another embodiment, the thermochromic dyes may be incorporated into a solid glycerine soap. Glycerine soap typically contains glycerine combined with conventional soap materials, such as tallow and lye in addition to an alcohol, such as a fatty alcohol, and a sugar. Glycerine soaps can be translucent when formed.

It should be understood, that the solid cleansing compositions as described above including solid soaps, solid cleansers, and glycerine soaps, can contain various other additives as desired. For instance, various oils, moisturizers, fragrances, dyes, preservatives, and other cosmetic ingredients may be contained within the product.

The present disclosure may be better understood with reference to the following examples.

EXAMPLE 1

The following is one example of a cleansing composition, such as a hand soap composition, that may be made in accordance with the present disclosure.

Exemplary Formulation

|  | Trade Name | % Weight | Supplier |
|---|---|---|---|
| Phase A | Water | 82.5 | USP |
|  | AQUA SF-1 | 4.0 | Noveon |
|  | MACKADET EY-191 | 10.0 | McIntyre Group, Ltd. |
| Phase B | KOH 10% Solution | pH 6.8 to 7.1 | Aldrich |
| Phase C | PARAGON 2 | 0.50 | McIntyre Group Ltd. |
|  | Thermochromic Dye |  |  |

-continued

| Trade Name | % Weight | Supplier |
|---|---|---|
| 29° C. Blue 50% slurry | 1.0 | Chromatic Technologies, Inc. |
| 32° C. Blue 50% slurry | 1.0 | Chromatic Technologies, Inc. |
| 35° C. Blue 50% slurry | 1.0 | Chromatic Technologies, Inc. |

As shown above, the hand soap composition contains three thermochromic dyes. The first thermochromic dye changes color at 29° C., the second thermochromic dye changes color at 32° C., while the third thermochromic dye changes color at 35° C. Thus, a color change occurs every 3° C. starting at 29° C.

In the above table, AQUA SF-1 is a suspending agent and comprises a crosslinked acrylic polymer. MACKADET EY-191 is a premixed soap formulation containing 40% solids of cocamidopropyl betaine, PEG-80 sorbitan laurate, sodium trideceth sulfate, citric acid, DMDM hydantoin, and tetrasodium EDTA.

Paragon 2, on the other hand, is a preservative blend containing propylene glycol as a non-aqueous solvent in combination with DMDM hydantoin, methylparaben and propylparaben.

In order to combine the above ingredients into a hand soap composition, Phase A was first blended together. The pH of the composition was then adjusted and Phase C was added and mixed until homogenous.

The above hand soap composition was tested. The soap composition was dispensed between the hands of a user and changed from a blue color to being substantially clear. The blue color remained until the composition reached a temperature of 35° C. At 35° C., the composition then turned clear. More particularly, the hand soap composition changed from a vibrant colored foam to a white foam when rubbed between the hands. By using a plurality of thermochromic dyes, the color change occurred quickly and continued until sufficient time had passed to indicate to a user that the hands had been sufficiently washed.

EXAMPLE 2

The following is another example of a cleansing composition, such as a hand soap composition, that may be made in accordance with the present disclosure.

Exemplary Formulation

| | Trade Name | % Weight | Supplier |
|---|---|---|---|
| Phase A | Water | 87.0 | USP |
| | Laponite XLG | 1.0 | Southern Clay Products |
| | MACKADET EY-191 | 10.0 | McIntyre Group, Ltd. |
| Phase B | KOH 10% Solution | pH 6.5 to 7.0 | Aldrich |
| Phase C | Germaben II | 0.5 | ISP |
| | Thermochromic Dye | | |
| | 29° C. Blue 50% slurry | 0.5 | Chromatic Technologies, Inc. |
| | 32° C. Blue 50% slurry | 0.5 | Chromatic Technologies, Inc. |
| | 35° C. Blue 50% slurry | 0.5 | Chromatic Technologies, Inc. |

Similar to the composition described in Example No. 1, the above composition also contains three thermochromic dyes.

In order to combine the above ingredients into a hand soap composition, Phase A was first blended together. The pH of the composition was then adjusted and Phase C was added and mixed until homogenous. As shown above, in this embodiment, clay particles were added as a suspending agent.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed:

1. A cleansing composition consisting of:
   at least one surfactant;
   at least two thermochromic dyes wherein each dye undergoes a color change at a different temperature blended with the surfactant, the thermochromic dyes changing the color of the cleansing composition when the composition reaches a temperature of from about 21° C. to about 40° C.;
   water from about 40% to about 99% by weight; and
   a suspending agent selected from the group consisting of a clay, a starch, a starch derivative, carboxymethyl cellulose, hydroxyethyl methyl cellulose, hydroxyethyl cellulose, guar gum, pectin, gum Arabic, locust bean gum, carrageenan gum, a multifunctional alcohol that is solid at 70° F., colloidal or fumed particles, a polyoxyethylene glycol fatty acid ester, a polyoxyethylene glycol ether and mixtures thereof;
   optionally, at least one sequestrant selected from the group consisting of ethylenediamine, ethylenediaminetetraacetic acid or salt thereof, polyphosphate, organophosphate, dimercaprol, and mixtures thereof;
   optionally, at least one emollient;
   optionally, at least one basic pH modifier;
   optionally, at least one fragrance;
   optionally, at least one antimicrobial agent; and
   optionally, at least one preservative.

2. A cleansing composition as defined in claim 1, wherein the suspending agent consists of a clay.

3. A cleansing composition as defined in claim 2, wherein the clay is a laponite clay.

4. A cleansing composition as defined in claim 2, wherein the clay is selected from the group consisting of a montmorillonite clay, a hectorite clay, an attapulgite clay, a smectite clay, a saponite clay, a laponite clay, and mixtures thereof.

5. A cleansing composition as defined in claim 1, wherein the suspending agent consists of a starch.

6. A cleansing composition as defined in claim 1, wherein the suspending agent is a starch derivative.

7. A cleansing composition as defined in claim 1, wherein the suspending agent consists of colloidal or fumed silica particles.

8. A cleansing composition as defined in claim 1, wherein the suspending agent is polyoxyethylene glycol ether or polyoxyethylene glycol fatty acid ester selected from the group consisting of a polyoxyethylene glycol distearate, a polyoxyethylene glycol diisostearate, a polyoxyethylene glycol pentaerythrityl tetrastearate, a methyl glucose dioleate, a polyoxyethylene glycol methyl glucose distearate, a polyoxyethylene glycol methyl glucose laureate, a polyoxyethylene glycol methyl glucose sesquistearate, a polyoxyethylene glycol stearate, and mixtures thereof.

9. A cleansing composition as defined in claim 1, wherein the suspending agent is the multifunctional alcohol that is an unmodified polyoxyethylene glycol polymer.

10. A cleansing composition as defined in claim 1, wherein the suspending agent is present in the composition in an amount from about 0.1 percent to about 15 percent by weight.

11. A cleansing composition consisting of:
  at least one surfactant; and
  a plurality of thermochromic dyes blended with the surfactant, the thermochromic dyes being present in an amount sufficient to add color to the cleansing composition, the thermochromic dyes also being present in an amount sufficient to cause the cleansing composition to change color once the composition has reached a selected temperature and wherein each of the plurality of thermochromic dyes undergoes a color change at a different temperature and are further configured to cause the cleansing composition to continue to change color over a temperature range of at least about 3° C. once the composition is heated to the selected temperature;
  water from about 40% to about 99% by weight;
  a suspending agent selected from the group consisting of a clay, a starch, a starch derivative, carboxymethyl cellulose, hydroxyethyl methyl cellulose, hydroxyethyl cellulose, guar gum, pectin, gum Arabic, locust bean gum, carrageenan gum, a multifunctional alcohol that is solid at 70° F., colloidal or fumed particles, a polyoxyethylene glycol fatty acid ester, a polyoxyethylene glycol ether and mixtures thereof;
  optionally, at least one sequestrant selected from the group consisting of ethylenediamine, ethylenediaminetetraacetic acid or salt thereof, polyphosphate, organophosphate, dimercaprol, and mixtures thereof;
  optionally, at least one emollient;
  optionally, at least one basic pH modifier;
  optionally, at least one fragrance;
  optionally, at least one antimicrobial agent; and
  optionally, at least one preservative.

12. A cleansing composition as defined in claim 11, wherein the suspending agent consists of clay and the clay is selected from the group consisting of a montmorillonite clay, a hectorite clay, an attapulgite clay, a smectite clay, a saponite clay, a laponite clay, and mixtures thereof.

13. A cleansing composition as defined in claim 11, wherein the suspending agent consists of starch.

14. A cleansing composition as defined in claim 11, wherein the suspending agent consists of the multifunctional alcohol.

15. A cleansing composition as defined in claim 11, wherein the suspending agent is polyoxyethylene glycol ether or a polyoxyethylene glycol fatty acid ester selected from the group consisting of a polyoxyethylene glycol distearate, a polyoxyethylene glycol diisostearate, a polyoxyethylene glycol pentaerythrityl tetrastearate, a methyl glucose dioleate, a polyoxyethylene glycol methyl glucose distearate, a polyoxyethylene glycol methyl glucose laureate, a polyoxyethylene glycol methyl glucose sesquistearate, a polyoxyethylene glycol stearate, glyceryl stearate, glycol stearate, glycol distearate, and mixtures thereof.

16. A cleansing composition as defined in claim 11, wherein the suspending agent consists of colloidal or fumed silica particles.

* * * * *